United States Patent [19]

Matilainen et al.

[11] Patent Number: 4,603,979

[45] Date of Patent: Aug. 5, 1986

[54] PROCEDURE AND MEANS FOR MEASURING THE INTERNAL FRICTION OF LIQUID SUBSTANCES

[76] Inventors: Aarre Matilainen, Lohkopellontie 1 A 8, 00650 Helsinki; Mauri Luukkala, Haukilahdenranta 23 B 5, 02170 Espoo, both of Finland

[21] Appl. No.: 662,425

[22] PCT Filed: Feb. 1, 1984

[86] PCT No.: PCT/FI84/00011

§ 371 Date: Sep. 26, 1984

§ 102(e) Date: Sep. 26, 1984

[87] PCT Pub. No.: WO84/03146

PCT Pub. Date: Aug. 16, 1984

[30] Foreign Application Priority Data

Feb. 7, 1983 [FI] Finland ................ 830410

[51] Int. Cl.4 ............................................ G01N 25/00
[52] U.S. Cl. ........................................ 374/54; 374/45; 73/55
[58] Field of Search .............. 374/45, 54; 73/54, 55, 73/56, 204

[56] References Cited

U.S. PATENT DOCUMENTS

| Re. 17,841 | 10/1930 | Zimmerli | 73/55 |
|---|---|---|---|
| 1,586,948 | 6/1926 | Connet | 73/55 |
| 2,023,568 | 12/1935 | Albersheim et al. | 73/55 |
| 3,841,147 | 10/1974 | Coil et al. | 73/56 |
| 3,930,399 | 1/1976 | Munk | 73/55 |
| 4,067,230 | 1/1978 | Ball | 73/54 |
| 4,425,790 | 1/1984 | Bice et al. | 73/55 |
| 4,527,417 | 6/1985 | Pravda | 374/45 |

FOREIGN PATENT DOCUMENTS 0013594 7/1980 European Pat. Off. .
2015750 9/1979 United Kingdom .

Primary Examiner—Charles Frankfort
Assistant Examiner—Thomas B. Will
Attorney, Agent, or Firm—Steinberg & Raskin

[57] ABSTRACT

The object of the present invention is to measure the magnitude of the friction and coefficient of friction or liquids with high viscosity or internal friction, such as molten plastic mix, e.g. in extruders by increasing the velocity of flow in a special measuring sleeve by stepwise reducing the flow cross section, whereby the flow velocity increases stepwise in accordance with the laws of hydrodynamics. When flow thermometers are installed at the points of reduction, the increase of friction energy can be assessed by the increase of temperature. When the temperature changes can be measured, the quantities describing the friction are calculable. The meter is applicable in numerous different situation and types of apparatus in which measurement of the friction energy is desired.

5 Claims, 3 Drawing Figures

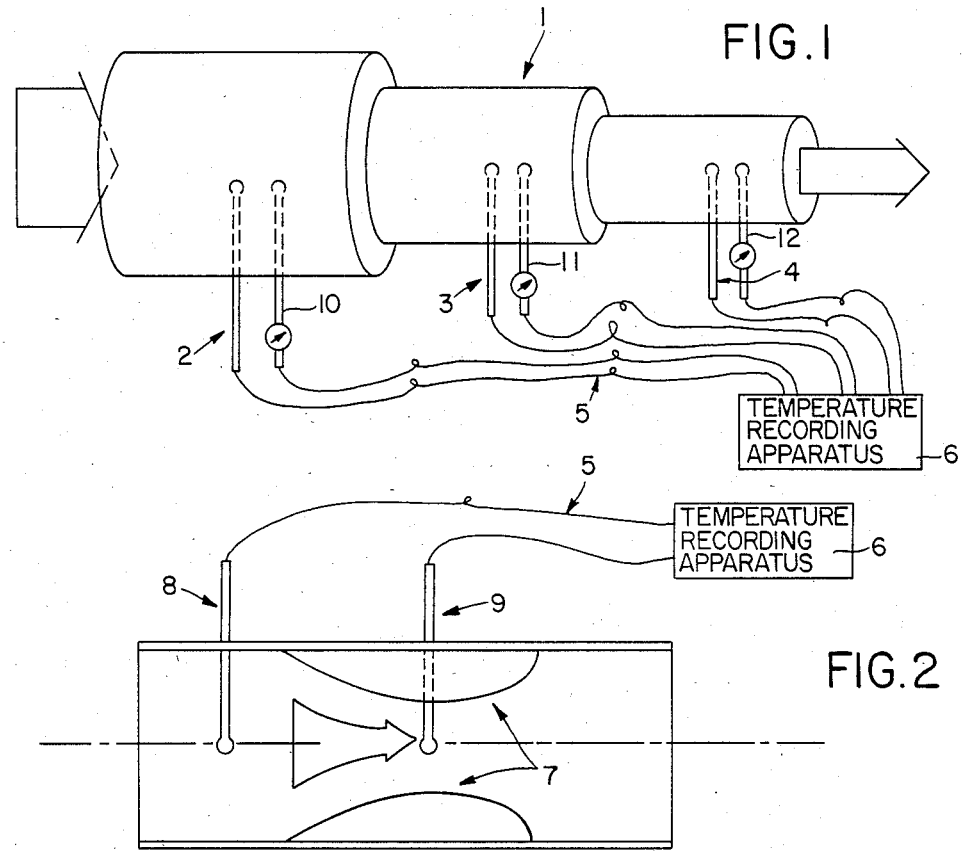
FIG.1
FIG.2
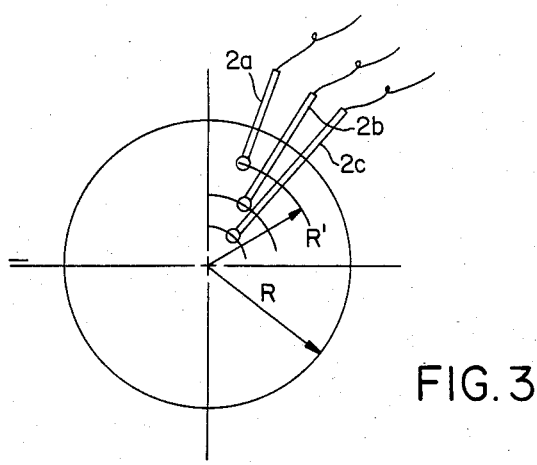
FIG.3

PROCEDURE AND MEANS FOR MEASURING THE INTERNAL FRICTION OF LIQUID SUBSTANCES

BACKGROUND OF THE INVENTION

The present invention concerns a procedure and a means for measuring the flowing friction of liquid substances with high internal friction and viscosity, such as molten plastic mix for instance.

Plastic extruders, or extrusion presses, are used to manufacture a huge variety of plastic components, such as tubes and pipes, sewer pipes of PVC, cable insulations of polyethylene, etc. In the extrusion process the granular raw material is placed under high pressure (200 bar) and high temperature (about 190°-230° C.) with a screw press and heating resistances. The molten plastic mix is then pressed through the nozzle or tool, being at the same time formed to become for instance a hollow tube, e.g. a sewer pipe. As a result of the high pressures and temperatures, quite remarkable amounts of energy have to be expended in extrusion processes. In the lack of reliable measuring pick-ups the extrusion process could not be fully optimized up to now. Optimization requires a reliable feedback as basis for control, but a continuously operating control loop could not be successfully implemented heretofore. This is because it has been found that measurement of temperature and pressure alone is not sufficient to base the control on. The state of the melt mass can be estimated to a certain degree by measuring the velocity of ultrasound through the mass, but this too does not disclose the height of friction in the extruder.

In order to optimize the energy consumption, one ought to know the amount of friction energy in the extrusion process. If the raw material is comparatively coarse hard PVC, the contribution of friction is assuredly high. Furthermore, the friction may also significantly depend on the degree of smoothness of the extruder walls. Although on the other hand conjectures are presented to the effect that the wall roughness has no effect on friction for the reason that close to the wall the velocity of the melt mass is low at all events. The flow profile of the melt mass is very poorly understood for the reason that practical measurements are very awkward.

SUMMARY OF THE INVENTION

We have in connection with a hard PVC manufacturing process made the following experiment. During extrusion pressing in progress, the operation of the extruder was stopped and the development of the temperature in the interior of the extruder was observed. Within less than one minute, the temperature had gone down about 10-15 degrees. This means that friction accounted for a fraction of this magnitude of the temperature of the melt mass, because when the mass stops moving, the friction energy falls out while the other kinds of heating remain in effect. The temperature reading was restored to its previous value about 10 seconds after restarting. This experiment demonstrates the high significance of friction in the temperature measurement.

The objects of the present invention are attained with the aid of a measuring sleeve shaped in a specific way and in which the melt mass is conveyed through a stepwise narrowing nozzle in such manner that its velocity stepwise increases in accordance with Bernoulli's law. The friction of the mass will thereby gradually increase as its velocity increases. When the temperature of the melt mass is measured in each reduced zone, the contribution of the friction terms can be assessed with the aid of thermometers alone. Since in each zone the pressure also changes as the velocity changes, it may also useful to measure the pressure in each zone. The advantages of a measuring sleeve of this kind is that its installation after the press section is easy; it is a completely passive measuring member; it interferes minimally with the flow; nothing but simple measuring pick-ups are used therein; and its price is quite moderate. Owing to the high pressures and frictions, high forces are produced which act on the temperature pick-ups and pressure pick-up inserted in the flow, but temperature and pressure pick-ups specially appropriate for use on extruders are available which tolerate the stresses involved.

In present-day extruders the temperature and pressure are observed of course, and they are employed in aid of the extrusion process setting, but these temperature and pressure values are only used as such because heretofore one has not understood estimating from them of the friction coefficients or the dependence of friction on the velocity or pressure of the mass. It is not even properly known whether, after all, careful grinding of the interior extruder surfaces is necessary or not. If the grinding step is omitted, this naturally implies considerable cost savings.

It is well known that the friction depends on velocity according to a certain law, in which the friction increases with a certain power of the velocity. The generation of the friction force may be represented by the equation $Q=\gamma v^x$, with Q standing for the friction energy, $\gamma$ for the coefficient of friction, v for the velocity of the melt mass, and x for an unknown power, which may be 2, 3 or even 5. It is known on the other hand that the friction energy is directly proportional to the temperature, whereby the changes of friction are elicited as changes of temperature. Therefore, measurements of the temperature at the different reductions of the nozzle are sufficient, although for the sake of perfection it is also worthwhile to measure the pressure changes, because they may furnish useful additional information.

The reductions mentioned in the foregoing are something like funnel-shaped reductions. However, one may be able to manage with one single reduction which constitutes in the sleeve a so-called Venturi tube, in which the increase of velocity is exactly known in accordance with Bernoulli's law.

Of the state of art, U.S. Pat. No. 3,841,147 may be mentioned. Therein is described an apparatus set-up wherein is measured the power expended in extrusion processing and with the aid of temperature measurement of the molten plastic mass, the energy departing from the process, and with the aid of the energy differential thus found, the viscosity is determined. Although this U.S. Patent endeavours to measure the viscosity of the melt mass, it is not within the sphere of the present invention since the essential point of the invention is a particular measuring sleeve containing reductions, by which one expressly aims to correct the erroneous readings of the thermometers caused by the moving melt mass. It is not possible with the mentioned U.S. Patent to measure the coefficient of friction or the power x. In actual fact, the procedure of said U.S. Patent may yield incorrect results as it fails to take into account the attrition temperature between the mass and the pick-up, among other things.

In U.S. Pat. No. 3,930,399 is disclosed an arrangement wherein in a special measuring cell is intentionally caused a flow resistance by means of some kind of porous plug, whereby the liquid loses energy to the flow resistance and the temperature of the liquid increases and its velocity goes down. From the differential temperature before and after the flow resistance, the viscosity of the liquid is calculated. In the present invention, no flow resistance is produced which would slow the velocity down and would tie up energy; instead, the flow is adiabatically accelerated in conformity with Bernoulli's law and taking into account the error of measurement incurred owing to frictions of different magnitude. In the U.S. Patent, the measuring velocities are different on both sides of the resistance and therefore contain an error term.

With the aid of the present invention, it is even possible to calculate the true temperature of the mass when the flow velocity approaches zero, and it differs hereby decisively from the said U.S. Patent.

BRIEF DESCRIPTION OF THE DRAWINGS

The invention is described in detail with reference to certain advantageous embodiments of the invention, presented in the figures of the attached drawings, but to which the invention is not meant to be exclusively confined.

In FIG. 1 is schematically presented the measuring sleeve to be mounted after the press section and which is composed of consecutive reductions with thermometers.

FIG. 2 depicts a similar arrangement in which the reduction consists of a Venturi tube.

FIG. 3 shows a cross section of a measuring sleeve with a plurality of thermometers radially at different points in the flow, in order that the temperature distribution at right angles to the flow might also be elicited.

DESCRIPTION OF THE PREFERRED EMBODIMENTS

In FIG. 1 is depicted a sleeve 1 having two consecutive reductions, although it would also be possible to operate with only one reduction. In this sleeve also three thermometers 2,3 and 4 have been mounted, which give the temperature readings $T_2, T_3$ and $T_4$. These thermometers may be, for instance, thermocouples which have been specifically developed for extrusion application. These thermometers have further been electrically connected with a measuring lead 5 to a temperature-recording instrument 6, which may be for instance a multi-channel recorder or equivalent. In measurements in practice, readings are taken for instance of the thermometers 2 and 4. From the potential relative increase of temperature the following expression is then obtained:

$$\frac{T_2 - T_4}{T_2} = \frac{\Delta T}{T_2} = \frac{\gamma V^x{}_2 - \gamma V^x{}_4}{\gamma V^x{}_2}$$

It is seen from this equation that since the coefficient of friction $\gamma$ appears both above and below the division line, it cancels out and the power x can be calculated.

It is obvious that other temperature pairs may also be used in order to gain additional accuracy, but the principle of measurement is clear from the preceding example. The coefficient of friction $\gamma$, again, is elicited from the circumstance that the increase of velocity, $V_2-V_4$, can be calculated by Bernoulli's law, since it is understood that the change of areas within the measuring sleeve is known. On the other hand, when the increase of temperature is known through measurement and the power x has been found, the friction coefficient $\gamma$ is immediately calculable. Pressure changes in the respective zones may also be measured by respective pressure pick-ups 10, 11, and 12 mounted in the sleeve next to the thermometers 2, 3, and 4.

In FIG. 2 is presented a measuring sleeve where instead of a plurality of consecutive reductions has been provided only one reduction of area and which has been shaped to constitute a so-called Venturi tube. A Venturi tube may be more advantageous regarding flow than several consecutive reductions. The requisite thermometers may be installed befor the Venturi tube and at the actual reduction 7 of the Venturi tube, where the flow velocity is highest. The readings from the thermometers 8 and 9 may then be used towards determining the friction parameters as in the example presented above.

FIG. 3 shows a cross section of a measuring sleeve where thermometers 2a, 2b, and 2c have been inserted to various depths in the direction of the radius R. This is because the temperature may vary considerably in radial direction. It is understood that the friction energy may contain two components: one, the friction between the molten mass and the wall and the other, arising from the proper viscosity of the molten mass. Close to the axis, the friction energy is probably due to the viscosity of the molten mass. It may be of paramount importance with a view to controlling an extrusion process to elicit the contribution from the proper viscosity of the mass. In the same manner, the contribution of so-called gliding agents can be elicited.

Measurements of the travelling time of ultrasound have been applied in order to elicit properties of the state of the melt mass. Accurate measurement of the ultrasonic time of travel yields some measured quantities related to the state of the mass, but separation e.g. of the contribution of viscosity unambiguously by means of ultrasonic measurements may be exceedingly awkward. It should be kept in mind that the velocity of ultrasound is a function of density, pressure, temperature, gliding modulus (compressibility) and viscosity. The method of measurement now under discussion elicits specifically the contribution of viscosity and friction. On the other hand it may be quite advantageous to combine measurements of the velocity of ultrasound and the friction measurements described here. It is thus also possible to mount ultrasonic pick-ups in the same measuring sleeve.

The measuring set-up of the invention may also be implemented in other flow and extrusion processes in which the contribution of friction and viscosity is high, not only in extruding plastics.

We claim:

1. A method of measuring flow friction of a liquid substance with high internal friction and viscosity, such as molten plastic mix, said liquid substance flowing in a special flow measuring sleeve having a flow area, and said liquid substance having a flow velocity, said method comprising the steps of;

stepwise increasing said flow velocity by stepwise reducing said flow area of said measuring sleeve, mounting a thermometer in the flow of said liquid substance upstream of the reduced flow area and mounting a thermometer in the flow of said liquid substance within the reduced flow area or areas, measuring temperature changes caused by an increase of flow friction within said reduced flow area or areas, and using said temperature changes to determine the flow friction of said liquid substance.

2. A meter for measuring flow friction of substances with high viscosity or internal friction, such as molten plastic mix, said meter comprised of a special measuring sleeve having consecutive reductions of flow cross sectional area which cause flow velocity, of said liquid substance, to increase stepwise along said measuring sleeve and thermometers mounted within the reductions of flow area and positioned so that an increase in temperature between two consecutive reduced flow areas may be measured, said thermometers being electrically connected to a temperature-recording apparatus, whereby an increase of friction energy, caused by the increase of flow velocity in said reduced flow areas, and other parameters related to the flow friction, such as a coefficient of friction, can be calculated by means which use said measured temperature increases and the increase of flow velocity in the reductions of flow area.

3. A meter according to claim 2, characterized in that the meter consists of a special measuring sleeve in which the velocity of the liquid or melt mass is increased by reduction of the cross sectional area of the sleeve, wherein the reduction constitutes a profiled Venturi tube, whereby the increase of friction energy and temperature caused by the increase of flow can be measured with the aid of at least two thermometers installed in the flow, where one of the thermometers is located before the reduction of the Venturi tube and the other of the thermometers is located in the Venturi tube at the point where the flow velocity is highest.

4. A meter according to claim 2, characterized in that the thermometers mounted in the measuring sleeve are located at different depths in a radial direction for the purpose of measuring the radial distribution of flow friction.

5. A meter according to claim 2 characterized in that on the side of the thermometers mounted in the measuring sleeve have been mounted pressure pick-ups measuring changes of pressure.

* * * * *